(12) United States Patent
Hanke et al.

(10) Patent No.: US 6,720,006 B2
(45) Date of Patent: Apr. 13, 2004

(54) ANTI-MICROBIAL BODY CARE PRODUCT

(76) Inventors: Bernhard Hanke, Breslaoerstrasse 12, Bad Schwalbach (DE), D-65307; Peter J. Guggenbichler, Hebelstrasse 4, Nurnberg (DE), D-90491

( * ) Notice: Subject to any disclaimer, the term of this patent is extended or adjusted under 35 U.S.C. 154(b) by 0 days.

(21) Appl. No.: 10/017,996

(22) Filed: Dec. 14, 2001

(65) Prior Publication Data
US 2002/0122832 A1 Sep. 5, 2002

(30) Foreign Application Priority Data

Jun. 17, 1999 (EP) .............................. 99111729
Jun. 9, 2001 (WO) ................. PCT/US00/15897

(51) Int. Cl.[7] .............. A61K 9/00; A61K 9/14; A61K 9/70; A61L 15/16; A01N 25/34
(52) U.S. Cl. .............. 424/484; 424/400; 424/402; 424/404; 424/443; 424/444; 424/447; 424/486; 424/487; 424/489
(58) Field of Search .............. 424/400, 402, 424/404, 443, 444, 447, 484, 486, 487, 489

(56) References Cited

U.S. PATENT DOCUMENTS

| 4,835,211 | A | * | 5/1989 | Noda et al. | 524/762 |
|---|---|---|---|---|---|
| 5,503,840 | A | * | 4/1996 | Jacobson et al. | 424/421 |
| 5,662,913 | A | * | 9/1997 | Capelli | 424/405 |
| 5,837,275 | A | * | 11/1998 | Burrell et al. | 424/409 |
| 6,153,210 | A | * | 11/2000 | Roberts et al. | 424/411 |
| 6,238,686 | B1 | * | 5/2001 | Burrell et al. | 424/423 |
| 6,475,631 | B1 | * | 11/2002 | Yamamoto et al. | 428/480 |

FOREIGN PATENT DOCUMENTS

| EP | 0 251 783 | * | 1/1988 |
|---|---|---|---|
| WO | WO 92/18098 | * | 10/1992 |

* cited by examiner

*Primary Examiner*—Thurman K. Page
*Assistant Examiner*—S. Tran
(74) *Attorney, Agent, or Firm*—Lott & Friedland, P.A.

(57) ABSTRACT

An anti-microbial body care product comprising in the part contacting the human or animal skin and/or mucosa and organic matrix containing homogeneously dispersed particles of a metallic silver having a particle size in the range of 1 to 50 nm (silver nanoparticles) in an amount providing on the surface of said part and anti-microbially effective but less than cytotoxic silver concentration. Preferred body care products are disposable absorbent articles, toothbrushes, cosmetic products and baby comforting products.

26 Claims, No Drawings

ANTI-MICROBIAL BODY CARE PRODUCT

CLAIM OF PRIORITY

This application is related to European Patent Office application Serial No. 99111729.2 filed on Jun. 17, 1999 and Patent Cooperation Treaty ("PCT") application Serial No. PCT/US00/15897 on Jun. 9, 2000, based upon which priority is claimed pursuant to 35 U.S.C. §§119(a) and 365(b).

TECHNICAL FIELD

The present invention relates to a body care product having anti-microbial activity, especially an anti-microbial disposable absorbent article, toothbrush, cosmetic product or baby comforter.

BACKGROUND OF THE INVENTION

Body care products are products which are brought into contact with human or animal skin and/or mucosa to provide a cleaning, protective, therapeutic, cosmetic benefit or soothing. Such products, for example disposable absorbent articles, such as diapers, incontinence articles, catamenial devices, training pants, panty liners, toothbrushes or baby comforters etc. normally comprise surfaces contacting the skin made of a natural or often synthetic polymeric material, or skin care compositions such as emulsions, lotions, creams, ointments, salves, powders, suspensions, gels, soaps, etc. Said products comprise either a polymer or an organic component in the carrier base, which is a good substrate for a number of microorganisms. The growth of such microorganisms on theses substrates may cause hygienic and medical problems.

It is already known to impregnate or coat such solid substrates with anti-microbial agents or disinfectants or to incorporate such active agents into said cosmetic bases to provide an anti-microbial activity. However, this method has only been a partial success. Continued sub-inhibition of chemically active substances induces resistance to microorganisms and thus, sensibilisation. The efficacy is limited to a certain range of germs and the activity is only of short-term.

It is already known as well to use silver in various forms as an anti-microbial agent, however, it is a serious problem to find the most appropriate delivery system.

For example there have been numerous attempts incorporate silver into various polymer articles, such as pipes, medical components, films, fibers, with varying degrees of success. For example this technology is subject-matter of U.S. Pat. No. 5,180,585, which discloses an anti-microbial composition comprising an inorganic particle with a first coating providing anti-microbial properties and a second coating providing a protective function.

European patent number EP0711113 discloses a process for producing bactericidal/fungicidal plastic bodies which comprises coating a plastic blank with one or more anti-microbially active metal(s) and/or metal compound(s) by means of a chemical or physical process, then grinding and/or melting said coated blank and finally imparting the desired shape to said material. In this way medical catheters of polyurethane comprising silver particles having a particle size below 100 nm, preferably of 10 nm, in an amount of not more than 1.0% by weight have been made.

However, it has also been found that silver ions while having an anti-microbial and anti-fungal activity are problematic once they are kept for a longer time at a high concentration in contact with the human skin or mucosa, because of their potential cytotoxicity.

The problem underlying the present invention therefore is to provide for a body care product that can be kept in contact with the human or animal skin or mucosa for a longer time during its normal use and which provides the desired anti-microbial activity without detrimental effects on the person using that product.

SUMMARY OF THE INVENTION

The above problems are solved by the body care product invention disclosed and claimed herein and by the preferred embodiments thereof, namely disposable absorbent articles, toothbrushes, cosmetic products and baby comforters.

Subject-matter of the present invention, therefore, is an anti-microbial body care product comprising in the part contacting human or animal skin and/or mucosa an organic matrix containing homogeneously dispersed particles of metallic silver having a particle size in the range of 1 to 50 nm (in the following termed "silver nanoparticles") in an amount providing on the surface of said part an anti-microbially effective but less than cytotoxic silver concentration.

DESCRIPTION OF THE PREFERRED EMBODIMENTS

It has been surprisingly found that a body care product comprising a surface contacting human or animal skin and/or mucosa shows an excellent tissue compatibility by not providing any cytotoxicity and is active against a broad range of microbes without any indication of resistance because of the very small quantities of silver released from the surface of said body care product over a long period. Based on this the body care product of the present invention is ideally suited for applications, wherein during normal use said product is in contact with the human or animal skin and/or mucosa for a longer period of time, by preventing irritation of the skin of the user and any negative changes to the skin structure.

For the purpose of the present invention, anti-microbial efficacy, i.e. activity against a broad range of microbes, may be quantified for example by methods such as described in *Der Erlanger Silberkatheter: In-vitro Ergebnisse zur antimikrobiellen Wirksamkeit* in Infection 26 (1998) Suppl. 1, German edition, pages 25 through 31.

For the purpose of the present invention, cytotoxicity may be quantified for example by methods such as described in *Untersuchung der akuten Zytotoxizität des Erlanger Silberkatheters zur Bestimmung der Biokompatibilität* in Infection 26 (1998) Suppl. 1, German edition, pages 36 through 39.

According to a preferred embodiment of the present invention, said silver nanoparticles are dispersed in said organic matrix in such an amount that a silver concentration of from more than 1 nmol/l to less than 1 $\mu$mol/l is provided, specifically when in contact with body fluids present on the surface of the human or animal skin and/or mucosa.

Preferably said organic matrix in contact with the human or animal skin comprises said silver nanoparticles in an amount from 1 to 2000 ppm, preferably from 5 to 1000 ppm and more preferably from 10 to 250 ppm.

The silver nanoparticles homogeneously dispersed in said organic matrix preferably have a particle size of 2 to 10 nm, more preferably of 5 to 8 nm.

The organic matrix into which said silver nanoparticles are homogeneously dispersed can be solid or fluid. The term fluid includes liquid and semisolid and covers a viscosity range of from 5 to 5000 mPa, preferably 5 to 500 mPa measured at 60° C. using a rotational viscosimeter (such as a Brookfield viscosimeter) at 60 rpm using a number 2 spindle.

In case the organic matrix is a solid material, it preferably comprises an organic polymer wherein said silver nanoparticles are homogeneously dispersed.

Said organic polymer of the solid organic matrix preferably comprises a thermoplastic resin, such as a polyamide, polyether, polyester, polyolefine, vinyl or (meth) acrylate homopolymer, copolymer or terpolymer, polyurethane and/or silicone rubber.

In incorporation of the silver nanoparticles into such polymers can be provided by making use of the method disclosed in EP0711113, supra, i.e. by coating a plastic blank with silver by means of a chemical or physical process, grinding and/or melting said coated blank and finally providing a molded article out of this polymer containing the homogeneously dispersed silver nanoparticles.

According to a further embodiment of the present invention, the part of the body care products contacting human or animal skin and/or mucosa comprises a fluid organic matrix wherein said silver nanoparticles are homogeneously dispersed. Said fluid organic matrix preferably is a viscous organic fluid having a viscosity as referred to above and comprises preferably aliphatic or aromatic hydrocarbon, a mineral oil, petrolatum, glycerol, a fatty alcohol, propylene glycol, polypropylene glycol, an animal and/or vegetable oil or fat or a silicone oil. Specifically preferred are silicone oils, i.e. polysiloxanes such as phenyl-functional-polymethylsiloxane compounds having a viscosity at 37° C. ranging from 5 to 5000 mPa, more preferably 5 to 2000 mPa, as measured with the viscosimeter preferred to above at a temperature of 37° C. A suitable silicone oil is available from Dow Corning Corporation, Michigan, USA, under the designation DC556 poly dimethyl silicone cosmetic grade (Dimethicone).

The incorporation of the silver nanoparticles can be done with an apparatus such as disclosed in German patent number 4440521 using a method involving the vacuum evaporation of metallic silver on a liquid in a vacuum chamber in which the organic fluid flows along the outside of a cylinder. This allows for the preparation of a liquid organic matrix comprising a homogenous extremely fine dispersion of silver nanoparticles having a particle size of about 5 nm. This silver-containing liquid organic matrix can be used to either coat the part of the body care product of the present invention contacting the skin and/or to impregnate or to incorporate by kneading into the material providing said surface, made of for example polyvinylbenzol, polyethylene, polypropylene or creamy oligomers, such as white petrolatum.

In the following preferred embodiments of the body care product of the present invention are described more in detail.

One specifically preferred embodiment thereof comprises a disposable absorbent article, i.e. a device which absorbs and contains body exudates, and, more specifically, devices which are placed against or in proximity to the body of the wearer to absorb and contain the various exudates discharged from the body. Examples of such disposable absorbent articles are diapers, incontinence articles, catamenial devices, training pants or panty liners. Such absorbent articles normally comprise a liquid pervious topsheet facing the wearer's body, and absorbent core and/or a liquid impervious backsheet that faces the wearer's clothing. In accordance with the present invention said topsheet, backsheet or absorbent core or also an adhesive connecting said components is made of a polymer comprising the above defined solid organic matrix containing the homogeneously dispersed silver nanoparticles defined above comprising the defined particle size and concentration.

According to a further embodiment of this disposable absorbent article, the liquid pervious topsheet, the absorbent core and/or the liquid impervious backsheet is coated and/or impregnated with the above defined fluid organic matrix containing said homogeneously dispersed silver nanoparticles.

In this way the body contacting surface of said disposable absorbent article comprises silver nanoparticles in an amount providing on the surface on said part an anti-microbially effective but less than cytotoxic silver concentration and thus exerts an anti-microbial or anti-fungal effect without negatively impacting the wearer's comfort, causing negative changes to the wearer's skin structure and without providing skin irritation. This is a substantial benefit, because in contrast to normal disinfectant agents, the silver nanoparticles are very effective in their anti-microbial activity and not irritating and thus can also be used in contact with the very sensitive skin of babies wearing such diapers for a longer time. Because the infection with and the propagation of microorganisms can be substantially prevented without irritating the skin, the absorbent articles of the present invention specifically diapers and incontinence articles, which are kept in contact with the skin surface for a longer term provide for a substantial improvement over the prior art products of this type.

Said topsheets normally are manufactured from a wide range of materials, such as woven and non-woven materials (e.g., a non-woven web of fibers); polymeric materials such as apertured formed thermoplastic films, apertured plastic films, and hydroformed thermoplastic films; porous foams, reticulated foams; reticulated thermoplastic films; and thermoplastic scrims. Suitable woven and non-woven materials can be comprised of natural fibers (e.g., wood or cotton fibers), synthetic fibers (e.g., polymeric fibers such as polyester, polypropylene or polyethylene fibers) or from a combination of natural and synthetic fibers. Said topsheet may comprise a single layer or more than one layer of material.

The absorbent core may comprise a variety reality of liquid absorbent or liquid handling materials commonly used in disposable diapers and other absorbent articles such as, but not limited to, comminuted wood pulp which is generally referred to as airfelt; meltblown polymers including coform; chemically stiffened, modified or crosslinked cellulosic fibers; tissue including tissue wraps and tissue laminates, other porous materials, such as foams, either alone or in combination with such fibers webs or fibrous materials which form a fibrous web or a fibrous matrix. Fibers useful therefor include naturally occurring fibers, such as wood or cotton fibers, modified or unmodified or synthetic fibers such as polyethylene and polypropylene fibers.

Optionally, the absorbent structure can comprise super absorbent polymers, or hydrogels. The hydrogel-forming absorbent polymers useful in the present invention include a variety of substantially water-insoluble but water-swellable polymers capable of absorbing large quantities of liquids. Such polymer materials are commonly referred to as "hydrocolloids", or "superabsorbent" materials. Such materials are known to the person skilled in the art.

The backsheet may comprise a material which is impervious to liquids but preferably sufficiently permeable to gases. Suitable materials thereof are polyethylene films, preferably microporous polyethylene films or films or composites which comprise a mixture of a block co-polyester, a block co polyetheramide and/or polyurethane, a thermoplastic homo-, co- or terpolymer etc.

A further preferred embodiment of the present invention comprises a toothbrush wherein the bristles and/or the handle are made of a polymer comprising said solid organic matrix containing said homogeneously dispersed silver nanoparticles with the defined particle size and concentration. It is also possible to impregnate and/or coat the bristles and/or the handle of said toothbrush with the above defined organic fluid matrix comprising said homogeneously dispersed silver nanoparticles. In this way the toothbrush is consistently provided with an anti-microbial effect without causing any irritation of the mucosa of the mouth. This is specifically important, because it has been found that for example bacterial A-streptococci can harbor within the polymer bristles of the toothbrush, so that a re-infection of the gingiva is caused. This can be prevented by incorporating said silver nanoparticles into the polymer bristles of the toothbrush according to this embodiment of the present invention.

According to a still further preferred embodiment the present invention, comprises a body care product in the form of a cosmetic composition comprising in its carrier base the above defined fluid organic matrix comprising said homogeneously dispersed silver nanoparticles. This cosmetic composition can be a cream-emulsion, suspension, lotion, ointment, salve, gel, powder, makeup, mascara, wipe, cleansing fluid, plaster, disinfecting fluid or toothpaste. It comprises a homogenous dispersion of the above defined silver nanoparticles in the organic phase of the carrier base of said products. Since the particle size of the silver nanoparticles dispersed is so small, there is no discoloration of the skin, so that the infection of such cosmetic compositions by microorganisms can be safely prevented without disturbing the desired cosmetic effect obtained.

The invention is disclosed more in detail on the basis of the following examples:

EXAMPLE 1

Using a plasma coating equipment polypropylene films measuring approximately 80 cm in width, 1000 m in length and 0,2 mm in thickness were evaporation treated to produce a 10 nm silver coating. This coated film was shredded and remolded at 220° C. into granules. They demonstrated a yellowish tint whereas the physical parameters remained mostly unchanged.

This material was made into topsheets for a diaper containing approximately 2000 ppm silver. An ELISA (enzyme-linked immuno-sorbent assay) measurement demonstrated an activity of this material against *Staphylococcus epidermidis* and *Candida albicans*.

EXAMPLE 2

A suspension containing silver nanoparticles with an individual size range of 5 to 50 nm was produced through thermal evaporation of silver into a liquid silicone oil base. Polypropylene granules ere then co-extruded with this silicone oil using a Werner & Pfleiderer equipment comprising a double extrusion coil with 33 mm diameter and cog elements, in order to produce further polypropylene granules containing up to 5% of the silver containing silicone oil. The granules exhibit a grayish-brown tint with no change the physical parameters of the polypropylene.

This master material was made into topsheets for diapers containing approximately 1000 ppm silver. The ELISA measurements demonstrated antibacterial efficacy.

EXAMPLE 3

A silver lotion comprising silver nanoparticles in white petrolatum and stearyl alcohol was prepared according to the method disclosed in Example 2. The composition of this silver nanoparticles containing lotion is as follows:

| Component | % by weight |
|---|---|
| 1) White Petrolatum | 57.8 |
| 2) Stearyl Alcohol | 40.9 |
| 3) Aloe extract in mineral oil | 1.1 |
| 4) Silicone oil containing 1 w/w % of Silver* | 0.1 |
| 5) Fumed Silica | 0.1 |

*The silicone oil is a cosmetic grade polyphenylmethylsiloxane containing 1% by weight of silver nanoparticles of a particle size in the range of 5 to 50 nm.

Firstly components 1, 2, 3 and 5 were put in a Stephan-mixer and heated under stirring up to 80° C. Thereafter the silver nanoparticles containing the silicone oil was added in one portion and the dispersion homogenized for three minutes.

1 g. of this silver nanoparticle containing lotion was sprayed on the topsheets of diapers (Pampers Extra Dry available from The Procter & Gamble Company, Schwalbach, Germany).

Samples containing 50 and 250 ppm Silver in the lotion were tested for the efficacy again *Staphylococcus epidermidis* and *Candida albicans* (in vitro ELISA). The impregnation of the topsheet with the 50 ppm silver nanoparticles containing lotion provided a clear anti-microbial effect. The vitality of the germs was greatly reduced and proliferation considerably limited. The test with a five times higher silver concentration demonstrated that the germ was completely eliminated.

EXAMPLE 4

The above silicone oil comprising silver nanoparticles disclosed in Example 3 was added to a molten hotmelt adhesive while stirring for five minutes. Said adhesive containing 50 to 250 ppm silver was used to connect the components (topsheet, absorbent core, backsheet) of a disposable absorbent article and at the same time to provide for an anti-microbial effect.

EXAMPLE 5

The silicone oil containing the silver nanoparticles as referred to in Example 3 was incorporated into a silicone polymer rubber obtained by addition condensation and crosslinking providing a children comfort.

The children comfort or silencer demonstrated anti-fungal and antibacterial efficacy when containing 50 ppm silver nanoparticles when directly added into one component before crosslinking. The samples were placed on (non-nutrient) mineral salt agar and inoculated with a mixed fungal spore suspension of *Aspergillus niger* and *Penicillium pinophilium, Chaetomium globosum, Aureobasidium pullulans* and *Gliocladium virens*. After an incubation of 28 days at 28° C. no growth of any of the microorganism was observed.

EXAMPLE 6

A silver nanoparticles containing wipe lotion was prepared using the following components:

| Component | % by weight |
| --- | --- |
| 1) Propylene glycol | 3.50 |
| 2) Polyquarternium (Merquat 280, Merck, Germany) | 2.60 |
| 3) Cetareth and Stearylalcohol (Cremophor A6, BASF) | 1.60 |
| 4) Silicone suspension 30% (Fluka Chemie AG, Switzerland, Product No. 85390 Silicone antifoam) | 10.00 |
| 5) Silver (1% ww) containing silicone oil* | 0.25 |
| 6) Zinc oxide | 0.05 |
| 7) Water | 82.0 |

*The silver nanoparticles containing silicone oil disclosed in Example 3

An emulsion was prepared by combining components 1, 2, 3 and 7 under stirring while heating up to 70° C. Thereafter the mixture was cooled to 50° C. and then components 4, 5 and 6 were added in one portion and the combination was mixed to obtain a homogenous mass.

This wipe lotion comprising 25 ppm silver nanoparticles provides a preventive treatment for diaper rash due to the reduction of Candida albicans and/or *Staphylococcus epidermidis* on the skin. The in vitro measurement demonstrated a total anti-microbial efficacy against *Staphylococcus epidermidis* and *Candida albicans*.

EXAMPLE 7

A cream without preservatives was manufactured in a usual way. While cooling down the above silver nanoparticles containing silicone oil of Example 3 was added at a temperature of 40° C. or less. An antibacterial activity over a silver concentration range of 10 to 500 ppm silver could be determined.

EXAMPLE 8

A usual toothpaste composition was prepared to which the same silver nanoparticles containing silicone oil used in Example 2 was added at a temperature of 40° C. or less providing a silver concentration of 10 to 500 ppm.

EXAMPLE 9

The same silver nanoparticles containing silicone oil was incorporated as the essential agent in a usual roll-on deodorant formulation. The deodorant did not destroy the microflora of the skin, however, the number of "cornyo formic" microorganisms responsible for body odor was selectively reduced. To avoid disturbing natural perspiration no conventional aluminum compounds were used. Surprisingly instead a synergistic effect and light astringency was achieved by adding zinc oxide.

The composition of this roll-on deodorant formulation is as follows:

| Component | % by weight |
| --- | --- |
| 1) Demineralized water | 88.2 |
| 2) Silicone suspension 30% (Fluka Chemie AG, Switzerland, Product No. 85390 Silicone antifoam) | 4.5 |
| 3) Cetheareth 6 and stearylalcohol (Cremophor BASF) | 4.5 |
| 4) Polyquarternium (Merquat 280, Merck) | 1.5 |
| 5) Cremophor A25, BASF | 0.3 |

| Component | % by weight |
| --- | --- |
| 6) Silver nanoparticles containing silicone oil* | 0.5 |
| 7) Zinc oxide | 0.5 |

*cf. Example 3

The deodorant was prepared by adding components 3 and 5 and melting the material in a water bath at 70° C. The de-mineralized water was heated up to 70° to 80° C., cooled down to approximately 50° and added to components 3 and 5. Thereafter immediately components 2, 6 and 7 were added and mixed using a mixer (Polythron) for four minutes at a speed of 2000 to 3000 min$^{-1}$.

Thereafter component 4 was added and the material was cooled down to room temperature while stirring at 300 to 4000 min$^{-1}$.

A silver grayish, whitish marbled dispersion with a faint characteristic odor is formed.

What is claimed is:

1. An anti-microbial body care product comprising in the surface contacting human or animal skin and/or mucosa an organic matrix containing homogeneously dispersed particles of metallic silver (silver nanoparticles) in an amount of 1 to 2000 ppm and having a particle size in the range of 1 to 50 nm providing on said surface an anti-microbially effective but less than cytotoxic silver concentration wherein irritation to the skin and negative changes to the skin structure of the user are prevented.

2. The body care product according to claim 1, characterized by comprising said silver nanoparticles in an amount providing a silver concentration of from more than 1 nmol/l to less than 1 $\mu$mol/l.

3. The body care product according to claim 2, characterized by comprising silver nanoparticles having a particle size of 2 to 10 nm.

4. The body care product according to claim 1, characterized in that said organic matrix is solid or fluid.

5. The body care product according to claim 4, characterized in that said solid organic matrix comprises an organic polymer wherein said silver nanoparticles are dispersed.

6. The body care product according to claim 5, characterized in that said organic polymer comprises a thermoplastic polyamide, polyether, polyester, polyolefine, vinyl or (meth)acrylate homopolymer, copolymer or terpolymer, polyurethane and/or silicone rubber.

7. The body care product according to claim 6, characterized in that the part contacting human or animal skin and/or mucosa is made of or coated with said solid organic matrix wherein said silver nanoparticles are dispersed.

8. The body care product according to claim 4, characterized in that said fluid organic matrix comprises an organic fluid wherein said silver nanoparticles are dispersed.

9. The body care product according to claim 8, characterized in that said organic fluid comprises an aliphatic or aromatic hydrocarbon, a mineral oil, petrolatum, glycerol, a fatty alcohol, polypropylene glycol, an animal and/or vegetable oil or fat, or a silicone oil.

10. The body care product according to claim 9, characterized in that the part contacting human or animal skin and/or mucosa is impregnated and/or coated with said fluid matrix comprising said homogeneously dispersed silver nanoparticles.

11. The body care product according to claim 1, characterized in that it comprises a disposable absorbent article, wherein the liquid pervious topsheet that faces the wearer's body, the absorbent core, the liquid impervious backsheet that faces the wearer's clothing and/or any adhesive connecting said components is made of a polymer comprising said solid organic matrix containing said homogeneously dispersed silver nanoparticles.

12. The body care product according to claim 1, characterized in that it comprises a disposable absorbent article, wherein the liquid pervious topsheet that faces the wearer's body, the absorbent core and/or the liquid impervious backsheet that faces the wearer's clothing is coated and/or impregnated with said fluid organic matrix containing said homogeneously dispersed silver nanoparticles.

13. The body care product article according to claim 12, characterized in that the disposable absorbent article is a diaper, incontinence article, catamenial device, training pant or panty liner.

14. The body care product according to claim 1, characterized in that it comprises a toothbrush, wherein the bristles and/or the handle are made of a polymer comprising said solid organic matrix containing said homogeneously dispersed silver nanoparticles.

15. The body care product according to claim 1, characterized in that it comprises a toothbrush, wherein the bristles and/or the handle are impregnated and/or coated with said organic fluid matrix comprising said homogeneously dispersed silver nanoparticles.

16. The body care product according to claim 1, characterized in that it comprises a cosmetic composition, comprising in the carrier base said fluid organic matrix comprising said homogeneously dispersed silver nanoparticles.

17. The body care product according to claim 16, characterized in that said cosmetic composition is a cream, emulsion, suspension, lotion, ointment, salve, gel, powder, makeup, mascara, wipe, cleansing fluid, shampoo, plaster, disinfecting fluid, hair spray or toothpaste.

18. The body care product according to claim 1, characterized in that it comprises a baby comforter, made of a solid organic matrix containing said homogeneously dispersed silver nanoparticles.

19. The body care product according to claim 18, characterized in that the solid organic matrix of said baby comforter is a silicone rubber containing said homogeneously dispersed silver nanoparticles.

20. The body care product according to claim 2, characterized by comprising silver nanoparticles having a particle size of 5 to 8 nm.

21. The body care product according to claim 2, characterized in that said organic matrix comprises said silver nanoparticles in an amount of 5 to 1000 ppm.

22. The body care product according to claim 21, characterized by comprising silver nanoparticles having a particle size of 2 to 10 nm.

23. The body care product to according to claim 21, characterized by comprising silver nanoparticles having a particle size of 5 to 8 nm.

24. The body care product according to claim 2, characterized in that said organic matrix comprises said silver nanoparticles in an amount of 10 to 250 ppm.

25. The body care product according to claim 24, characterized by comprising silver nanoparticles having a particle size of 2 to 10 nm.

26. The body care product according to claim 24, characterized by comprising silver nanoparticles having a particle size of 5 to 8.

\* \* \* \* \*